United States Patent [19]

Junino et al.

[11] Patent Number: 5,145,483

[45] Date of Patent: Sep. 8, 1992

[54] SUBSTITUTED ORTHO-AMINOPHENOLS, PROCESS FOR PREPARING THEM AND THEIR USE FOR THE OXIDATIN DYEING OF KERATINOUS FIBRES

[75] Inventors: Alex Junino, Livry-Gargan; Hervé Andrean, Paris; Gérard Lang, Saint-Gratien, all of France

[73] Assignee: L'Oreal, Paris, France

[21] Appl. No.: 427,474

[22] Filed: Oct. 27, 1989

[30] Foreign Application Priority Data

Oct. 28, 1988 [FR] France .................. 88 14204

[51] Int. Cl.$^5$ .............................................. A61K 7/13
[52] U.S. Cl. .......................................... 8/412; 8/410; 8/411; 8/416; 8/421; 560/29; 564/182; 564/223
[58] Field of Search ............... 8/410, 411, 412, 416, 8/421; 560/29; 564/223, 182

[56] References Cited

U.S. PATENT DOCUMENTS

| | | | |
|---|---|---|---|
| 1,853,455 | 4/1932 | Reddelien | 564/223 |
| 1,878,543 | 9/1932 | Rimele | 564/182 |
| 1,901,322 | 3/1933 | Neelmeier | 564/182 |
| 3,250,763 | 5/1966 | Gies | 564/223 |
| 3,666,812 | 5/1972 | Kalopissis et al. | 8/421 |
| 3,738,799 | 6/1973 | Kalopissis et al. | 8/421 |
| 3,742,048 | 6/1973 | Gregoire et al. | 564/223 |
| 3,871,865 | 3/1975 | Teach | 564/223 |
| 3,948,596 | 4/1976 | Kalopissis et al. | 8/412 |
| 3,953,508 | 4/1976 | Kalopissis et al. | 8/410 |
| 3,961,879 | 6/1976 | Bigant et al. | 8/412 |
| 4,248,794 | 2/1981 | Fujii et al. | 564/223 |
| 4,370,142 | 1/1983 | Bigant et al. | 8/410 |
| 4,692,166 | 9/1987 | Junino et al. | 8/410 |
| 5,073,173 | 12/1991 | Pan et al. | 8/405 |

FOREIGN PATENT DOCUMENTS

| | | | |
|---|---|---|---|
| 0165564 | 12/1985 | European Pat. Off. | 564/223 |
| 3641825 | 6/1988 | Fed. Rep. of Germany . | |
| 1507886 | 12/1967 | France | 564/223 |
| 2421869 | 12/1979 | France | 8/421 |
| 7217741 | 7/1973 | Netherlands | 8/412 |

*Primary Examiner*—Paul Lieberman
*Assistant Examiner*—Linda D. Skaling
*Attorney, Agent, or Firm*—Fleit, Jacobson, Cohn, Price, Holman & Stern

[57] ABSTRACT

5-Substituted ortho-aminophenols of formula:

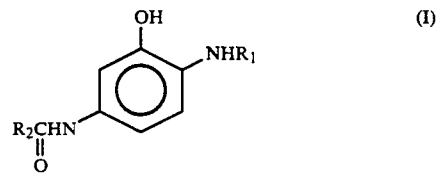

in which:

$R_1$ denotes a hydrogen atom, an alkyl radical having 1 to 4 carbon atoms or a hydroxyalkyl radical having 1 to 4 carbon atoms; and $R_2$ denotes, independently of $R_1$, an alkyl radical having 1 to 4 carbon atoms, an alkoxy radical having 1 to 4 carbon atoms or a benzyl radical;

the addition salts with an acid and the phenates, and dyeing composition containing a compound of formula (I) or a salt or a phenate of such a compound.

The 5-substituted ortho-aminophenols enable hair to be dyed in a rich spectrum of hues having good durability.

20 Claims, No Drawings

SUBSTITUTED ORTHO-AMINOPHENOLS, PROCESS FOR PREPARING THEM AND THEIR USE FOR THE OXIDATIN DYEING OF KERATINOUS FIBRES

The invention relates to 5-substituted ortho-aminophenols, to a process for preparing them and to their use in dyeing compositions for dyeing keratinous fibres, and especially human hair.

These dyeing compositions are used for the dyeing known as oxidation dyeing or permanent dyeing. This dyeing process enables keratinous fibres, in particular white hair, to be dyed in a large number of hues.

The dyeing of keratinous fibres by so-called oxidation dyeing is known. This dyeing employs oxidation dye precursors also referred to as oxidation bases, which are colourless but develop a long-lasting coloration in the keratinous fibres on contact with an oxidizing agent. As oxidation dye precursors, para-phenylenediamines, ortho-phenylenediamines, para-aminophenols and ortho-aminophenols, substituted or unsubstituted, are known. These oxidation dye precursors, hereinafter referred to as "precursors" may be mixed with one or more compounds referred to as "couplers". These couplers, generally selected from meta-diamines, meta-aminophenols, meta-diphenols and phenols, enable the hues which would be obtained with the precursor or precursors to be modified.

French Patent 2,460,664 and U.S. Pat. No. 4,370,142 describe dyeing compositions and a hair dyeing process based on para-phenylenediamine and ortho-aminophenol, in very particular ratios and in the absence of couplers, to obtain colours ranging from chestnut brown to black.

It has been discovered that ortho-aminophenols substituted at the 5-position, alone or in combination either with other precursors or with couplers or with both, enable keratinous fibres, and especially hair, to be dyed in a rich spectrum of colours which were not obtained with the compositions described in the above-mentioned patents.

The subject of the present invention is the new compounds comprising the 5-substituted ortho-aminophenols corresponding to the general formula (I) below, their addition salts with an acid and their phenates.

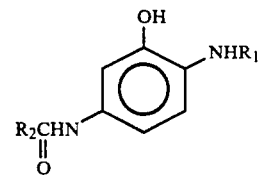

In this formula:

$R_1$ denotes a hydrogen atom, an alkyl radical having 1 to 4 carbon atoms or a hydroxyalkyl radical having 1 to 4 carbon atoms; and $R_2$ denotes, independently of $R_1$, an alkyl radical having 1 to 4 carbon atoms, an alkoxy radical having 1 to 4 carbon atoms or a benzyl radical.

Another subject of the invention is the use of the compounds of formula (I) or their addition salts with an acid or their phenates, either alone or in combination with couplers. In this case, the compounds of formula (I) play, in oxidation dyeing, the part of oxidation dye precursors. In combination with other precursors, the compounds of general formula (I) or their salts or their phenates play the part of couplers for the dyeing of keratinous fibres, and especially human hair.

The subject of the present invention is also a dyeing composition for keratinous fibres, and especially for human hair, comprising one or more compounds of formula (I) in an aqueous vehicle.

The dyeing compositions containing one or more compounds of formula (I), either alone or in combination with a precursor or a coupler, enable a wide variety of hues to be imparted to hair: varieties of hues ranging from blues to purples when the compound (I) is combined with a precursor selected from p-phenylenediamines, reds to oranges when it is combined with a precursor selected from p-aminophenols. Used alone or in combination with a "coupler", the compound (I) imparts to hair hues ranging from blonde and beiges to oranges.

Thus, the compounds of formula (I) offer the cosmetological chemist a rich spectrum of hues, making possible a great wealth of formulations.

The invention also relates to the process for preparing the compounds of formula (I):

The compounds of formula (I) are obtained by a four-stage process, according to the reaction scheme below, in which $R_1$ and $R_2$ have the meaning defined above and $B_z$ denotes benzyl.

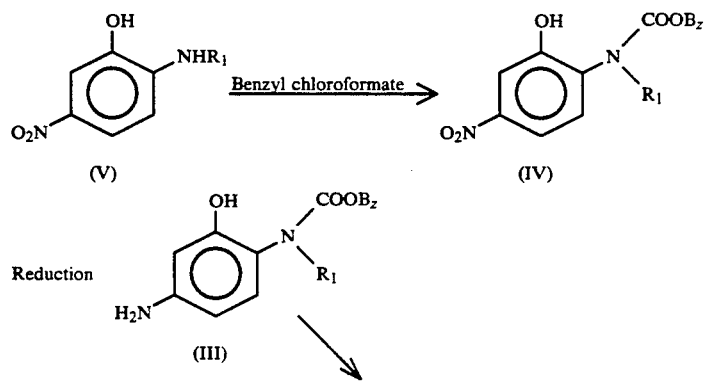

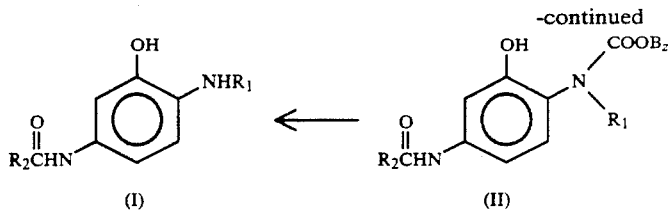

1st stage

The condensation of benzyl chloroformate with the aminonitrophenol of formula (V) is performed in a polar solvent such as dioxane, dimethylformamide, dimethyl sulphoxide or N-methylpyrrolidone, at a temperature not exceeding 100° C., in the presence of a trapping agent for hydrochloric acid which is preferably calcium carbonate.

2nd stage

The reduction of the nitrophenol of formula (IV) must be performed without causing cleavage of the benzyl carbamate. This reduction may be performed as follows:

(i) by catalytic hydrogenation using Raney nickel as a catalyst, in the presence of common solvents such as ethyl acetate or a $C_1$-$C_4$ alcohol and preferably ethanol, under a hydrogen pressure not exceeding $10^6$ pascals (10 bars);

(ii) reduction by hydrogen transfer using Raney nickel as a catalyst, hydrazine as a hydrogen donor and an aqueous-alcoholic mixture as a solvent;

(iii) reduction with sodium hydrosulphite, using water as a solvent;

(iv) reduction with iron/acetic acid, in a solvent such as water or ethanol.

These reduction reactions are performed at a temperature of between 20 and 100° C.

3rd stage

The acylation of the compound (III) is carried out by means of an acid chloride or an alkyl chloroformate or alternatively, when $R_2$ denotes an alkyl radical, acylation of the amino group with an acid anhydride.

4th stage

The cleavage of the benzyloxy radical is performed either by catalytic hydrogenation using palladium as a catalyst, or by hydrogen transfer using cyclohexene as a hydrogen donor in the presence of palladium.

These reactions are performed in an alcoholic or aqueous-alcoholic solvent, using a $C_1$-$C_4$ alcohol.

The latter reactions are described in "Protective groups in organic synthesis" by W. GREEN, publ. John Wiley, p. 239 (1981).

The invention is illustrated by the non-limiting preparation examples below.

PREPARATION EXAMPLE 1

Preparation of 5-acetamido-2-aminophenol hydrochloride

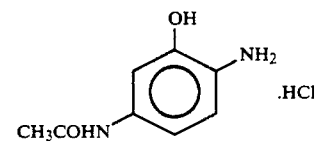

1st stage

Preparation of 2-(N-benzyloxycarbonylamino)-5-nitrophenol 3.58 moles (536 ml) of benzyl chloroformate (95%) are added in the course of 45 minutes to 3.25 moles (500 g) of 2-amino-5-nitrophenol and 204.5 g of calcium carbonate in 1.5 liter of dioxane brought to 70° C., the temperature being maintained at between 70° C. and 80° C. When the addition is complete, heating is maintained for a further 30 minutes. The inorganic salts present in the reaction medium are removed by filtration while hot. After the addition of ice-cold water to the filtrate, the expected product crystallizes. After filtration and drying, the product obtained is recrystallized from acetic acid. It melts at 200° C.

Analysis of the product obtained gives the following results:

| Analysis | Calculated for $C_{14}H_{12}N_2O_5$ | Found |
| --- | --- | --- |
| C | 58.33 | 58.38 |
| H | 4.20 | 4.17 |
| N | 9.72 | 9.69 |
| O | 27.75 | 27.60 |

2nd stage

Preparation of 5-amino-2-(N-benzyloxycarbonylamino)phenol 0.53 mole (153 g) of 2-(benzyloxycarbonylamino)-5-nitrophenol in 1 liter of ethanol is subjected to a hydrogen pressure of $8 \times 10^5$ pascals (8 bars) in an autoclave in the presence of 60 g of Raney nickel (water content 50%). After 1 hour at 65° C., the reaction medium is filtered while hot in order to remove the catalyst. On cooling the filtrate, the expected product crystallizes. After draining and drying, the product obtained is recrystallized in 96° strength ethanol. It melts at 148° C.

Analysis of the product obtained gives the following results:

3rd stage

Preparation of 5-acetamido-2-(N-benzyloxycarbonylamino)phenol 0.6 mole (57 ml) of acetic anhydride is added dropwise to a solution of 0.6 mole (172 g) of 5-amino-2-(benzyloxycarbonylamino)phenol in 465 ml of dioxane heated to 70° C. After the reaction medium is cooled, the expected product precipitates. When recrystallized in 96° ethanol, it melts at 205° C.

Analysis of the product obtained gives the following results:

| Analysis | Calculated for $C_{14}H_{14}N_2O_3$ | Found |
|---|---|---|
| C | 65.10 | 65.23 |
| H | 5.46 | 5.64 |
| N | 10.85 | 10.73 |
| O | 18.59 | 18.57 |

| Analysis | Calculated for $C_{16}H_{16}N_2O_4$ | Found |
|---|---|---|
| C | 63.99 | 63.85 |
| H | 5.37 | 5.52 |
| N | 9.33 | 9.18 |
| O | 21.31 | 21.58 |

4th stage

Preparation of 5-acetamido-2-aminophenol hydrochloride 0.6 mole (182 g) of 5-acetamido-2-(benzyloxycarbonylamino)phenol in 910 ml of absolute ethanol to which 310 ml of cyclohexene are added is brought to reflux in the presence of 91 g of palladinized charcoal (10% palladium; water content 50%). After 1 hour's reaction, the evolution of carbon dioxide ceases and the catalyst is removed by filtration while hot. The expected product is precipitated by adding 90 ml of ethanolic hydrochloric acid (7M) to the cooled filtrate.

Analysis of the product obtained gives the following results:

| Analysis | Calculated for $C_{14}H_{11}N_2O_2Cl$ | Found |
|---|---|---|
| C | 47.10 | 47.15 |
| H | 5.43 | 5.49 |
| N | 13.82 | 13.79 |
| O | 15.80 | 15.96 |
| Cl | 17.53 | 17.55 |

PREPARATION EXAMPLE 2

Preparation of 2-amino-5-(N-ethoxycarbonylamino)phenol hydrochloride hydrate

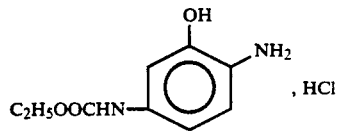

1st stage

Preparation of 5-(N-ethoxycarbonylamino)-2-(N-benzyloxycarbonylamino)phenol 0.14 mole (15.7 g) of ethyl chloroformate is slowly added dropwise to 0.13 mole (33 g) of 5-amino-2-(benzyloxycarbonylamino)phenol (prepared in Example 1, 2nd stage) and 7.1 g of calcium carbonate in 100 ml of dioxane brought to 80° C. The mixture is heated for a further 20 minutes after the addition is complete. The reaction mixture is filtered while hot in order to remove the inorganic salts. The expected product is precipitated by diluting the cooled filtrate with ice-cold water. When recrystallized from ethyl acetate, it melts at 190° C.

Analysis of the product obtained gives the following results:

| Analysis | Calculated for $C_{17}H_{18}N_2O_5$ | Found |
|---|---|---|
| C | 61.81 | 61.71 |
| H | 5.45 | 5.51 |
| N | 8.48 | 8.43 |
| O | 24.24 | 24.49 |

2nd stage

Preparation of 2-amino-5-(N-ethoxycarbonylamino)phenol 0.06 mole (20 g) of 5-(ethoxycarbonylamino)-2-(benzyloxycarbonylamino)phenol in 60 ml of 96° strength ethanol to which 40 ml of cyclohexene and 4 g of palladinized charcoal (10% palladium) are added is heated to reflux for 30 minutes. After removal of the catalyst by filtration while hot, the expected product is precipitated by adding 17.5 ml of ethanolic hydrochloric acid (7M) to the cooled filtrate. After drying, analysis of the product obtained gives the following results:

| Analysis | Calculated for $C_9H_{15}ClN_2O_4$ | Found |
|---|---|---|
| C | 43.12 | 43.20 |
| H | 6.03 | 6.58 |
| N | 11.17 | 11.23 |
| O | 25.53 | 24.67 |
| Cl | 14.14 | 14.20 |

PREPARATION EXAMPLE 3

Preparation of 2-amino-5-(N-benzylcarbonylamino)phenol hydrochloride

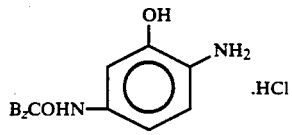

1st stage

Preparation of 2-(N-benzyloxycarbonylamino)-5-(N-benzylcarbonylamino)phenol 12 g of benzoyl chloride are slowly added dropwise to 0.77 mole (20 g) of 5-amino-2-(benzyloxycarbonylamino)phenol (prepared in the 2nd stage of Example 1) and 12 g of calcium carbonate in 120 ml of dioxane brought to 80° C. The mixture is heated for a further 20 minutes after the addition is complete. The mixture is filtered while hot in order to remove the inorganic salts. The expected product is precipitated by diluting the filtrate with ice-cold water. When recrystallized from methoxyethanol, it melts at 252° C.

Analysis of the product obtained gives the following results:

| Analysis | Calculated for $C_{22}H_{20}N_2O_4$ | Found |
|---|---|---|
| C | 69.23 | 69.46 |
| H | 5.49 | 5.54 |
| N | 7.69 | 7.65 |
| O | 17.58 | 17.46 |

2nd stage

Preparation of 2-amino-5-(N-benzylcarbonylamino)phenol hydrochloride 0.058 mole (22 g) of 2-(benzyloxycarbonylamino)-5-(benzylcarbonylamino)phenol in 66 ml of 96° ethanol to which 44 ml of cyclohexene and 4.4 g of palladinized charcoal (10% palladium) are added is heated to reflux for 35 minutes. After removal of the catalyst by filtration while hot, 30 ml of absolute ethanol and 17 ml of ethanolic hydrochloric acid (7M) are added to the cooled filtrate. The expected product precipitates. After drying, analysis of the product obtained gives the following results:

| Analysis | Calculated for $C_{14}H_{15}N_2O_2Cl$ | Found |
|---|---|---|
| C | 60.32 | 60.21 |
| H | 5.38 | 5.44 |
| N | 10.05 | 10.25 |
| O | 11.49 | 11.66 |
| Cl | 12.75 | 12.70 |

PREPARATION EXAMPLE 4

Preparation of 5-acetamido-2-[(β-hydroxyethyl)amino]-phenol hydrochloride

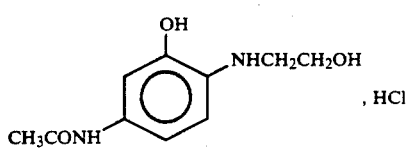

1st stage

Preparation of 2-N-benzyloxycarbonyl-N-(β-hydroxyethyl)amino]-5-nitrophenol 1.1 moles (197.7 g) of benzyl chloroformate are added to 1.1 moles (220 g) of 2-[(β-hydroxyethyl)amino]-5-nitrophenol and 61 g of calcium carbonate in 733 ml of dioxane brought to 70° C., the temperature being maintained at between 70 and 80° C. When the addition is complete, the temperature is maintained for one hour at 80° C. and the mixture is then allowed to cool to room temperature. The reaction mixture is then poured into 10 kg of ice-cold water and the resulting mixture is acidified with a strong acid. The expected product crystallizes. After filtration and drying, the product obtained is recrystallized from a mixture of cyclohexane and 1,2-dichloroethane. It then melts at 136° C.

Analysis of the product obtained gives the following results.

| | Analysis for $C_{16}H_{16}N_2O_6$ | | | |
|---|---|---|---|---|
| | C | H | N | O |
| Calculated | 57.83 | 4.82 | 8.43 | 28.91 |
| Found | 57.85 | 4.75 | 8.45 | 29.08 |

2nd stage

Preparation of 5-amino-2-[N-benzyloxycarbonyl-N-(β-hydroxyethyl)amino]phenol 0.24 mole (80 g) of 2-[N-benzyloxycarbonyl-N-(β-hydroxyethyl)amino]-5-nitrophenol in 630 ml of ethyl acetate is subjected to a hydrogen pressure of $9 \times 10^5$ pascals (9 bars) in an autoclave in the presence of 15 g of Raney nickel (water content 50%). After one hour at 85° C., the reaction medium is filtered while hot in order to remove the catalyst. On evaporation of the solvent under vacuum, the expected product crystallizes. After draining and drying, the product obtained is recrystallized from 96° strength alcohol It melts at 142° C.

Analysis of the product obtained gives the following results.

| | Analysis for $C_{16}H_{18}N_2O_4$ | | | |
|---|---|---|---|---|
| | C | H | N | O |
| Calculated | 63.57 | 5.96 | 9.27 | 21.19 |
| Found | 63.29 | 5.90 | 9.23 | 21.29 |

3rd stage

Preparation of 5-acetamido-2-[N-benzyloxycarbonyl-N-(β-hydroxyethyl)amino]phenol hemihydrate 0.24 mole (23 ml) of acetic anhydride is added dropwise to a solution of 0.24 mole (72 g) of 5-amino-2-[N-benzyloxycarbonyl-N-(β-hydroxyethyl)amino]phenol in one liter of ethyl acetate heated to 80° C. After evaporation of the solvent under vacuum, the expected product is purified on a silica column. It then melts at 72° C.

| Analysis for $C_{18}H_{21}N_2O_{5.5}$ | | | |
|---|---|---|---|
| | C | H | N | O |
| Calculated | 61.18 | 5.94 | 7.9 | 24.92 |
| Found | 61.57 | 5.93 | 7.88 | 24.80 |

4th stage

Preparation of 5-acetamido-2-[N-(β-hydroxyethyl)amino]phenol hydrochloride $5.8 \times 10^{-3}$ mole of 5-acetamido-2-[N-benzyloxycarbonyl-N-(β-hydroxyethyl)amino]phenol in 10 ml of 96° strength ethanol to which 6 ml of cyclohexene are added is brought to reflux in the presence of 0.35 g of palladinized charcoal (10% palladium; water content 50%). After one hour's reaction, the evolution of carbon dioxide ceases and the catalyst is removed by filtration while hot. The expected product is precipitated by adding 1.35 ml of ethanolic hydrochloric acid (7M) to the cooled filtrate.

Analysis of the product obtained gives the following results.

| Analysis for $C_{10}H_{15}N_2O_3Cl$ | | | | |
|---|---|---|---|---|
| | C | H | N | O | Cl |
| Calculated | 48.68 | 6.08 | 11.35 | 19.47 | 14.40 |
| Found | 48.67 | 6.15 | 11.20 | 19.68 | 14.30 |

PREPARATION EXAMPLE 5

Preparation of 5-acetamido-2-(methylamino)phenol hydrochloride

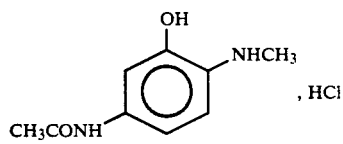

1st stage

Preparation of 2-(N-benzyloxycarbonyl-N-methylamino)-5-nitrophenol 0.26 mole (40 ml) of benzylchloroformate are added dropwise to 0.24 mole (41.5 g) of 2-methylamino-5-nitrophenol and 15.6 g of calcium carbonate in 125 ml of dioxane brought to 80° C., the temperature being maintained at between 80° C. and 95° C. When the addition is complete, heating is maintained for a further 2 hours. The inorganic salts present in the reaction medium are removed by filtration while hot. After the addition of ice-cold water, the expected product crystallizes. The product obtained is recrystallized from acetic acid. It melts at 192° C.

Analysis of the product obtained gives the following results.

| Analysis for $C_{15}H_{14}N_2O_5$ | | | |
|---|---|---|---|
| | C | H | N | O |
| Calculated | 59.60 | 4.63 | 9.27 | 26.49 |

| Analysis for $C_{15}H_{14}N_2O_5$ | | | |
|---|---|---|---|
| | C | H | N | O |
| Found | 59.56 | 4.65 | 9.28 | 26.53 |

2nd stage

Preparation of 5-acetamido-2-(N-benzyloxycarbonyl-N-methylamino)phenol $3.3 \times 10^{-2}$ mole (10 g) of 2-(N-benzyloxycarbonyl-N-methylamino)-5-nitrophenol is added to 40 g of iron powder in 60 ml of 96° strength ethanol mixed with 20 ml of acetic acid brought to 80° C., the temperature being maintained at 80° C. When the addition is complete, heating is maintained for 30 minutes. The inorganic salts present in the reaction medium are removed by filtration while hot. The filtrate is diluted with 800 ml of ice-cold water. $3.7 \times 10^{-2}$ mole (3.5 ml) of acetic anhydride is then added. The expected product crystallizes after 3 hours. After filtration and drying, the product obtained is recrystallized from a water/ethanol mixture. It then melts at 174° C.

Analysis of the product obtained gives the following results.

| Analysis for $C_{17}H_{18}N_2O_4$ | | | |
|---|---|---|---|
| | C | H | N | O |
| Calculated | 64.96 | 5.73 | 8.91 | 20.38 |
| Found | 64.97 | 5.75 | 8.87 | 20.39 |

3rd stage

Preparation of 5-acetamido-2-(methylamino)phenol hydrochloride $5.4 \times 10^{-3}$ mole (1.7 g) of 5-acetamido-2-(N-benzyloxycarbonyl-N-methylamino)phenol in 8.5 ml of 96° strength ethanol to which 5.1 ml of cyclohexene are added is brought to reflux in the presence of 0.35 g of palladinized charcoal (water content 50%). After one hour under reflux, the evolution of carbon dioxide ceases and the catalyst is removed by filtration while hot. The expected product is precipitated by adding 1.6 ml of ethanolic hydrochloric acid (7M) to the cooled filtrate.

Analysis of the product obtained gives the following results.

| Analysis for $C_9H_{13}N_2O_2Cl$ | | | | |
|---|---|---|---|---|
| | C | H | N | O | Cl |
| Calculated | 49.88 | 6.00 | 12.93 | 14.78 | 16.39 |
| Found | 49.77 | 6.07 | 12.78 | 14.90 | 16.28 |

The dyeing compositions for keratinous fibres, and especially for human hair, according to the invention, contain at least one compound of formula (I) in an aqueous vehicle.

The compounds of formula (I) are used in the compositions of the invention at concentrations of between 0.02 and 6%, and preferably between 0.15 and 5%, by weight relative to the total weight of the composition.

The compositions of the invention can also contain other oxidation dye precursors.

Among these oxidation dye precursors, para-phenylenediamines, para-aminophenols, ortho-phenylenediamines and ortho-aminophenols, and heterocyclic bases such as 2,5-diaminopyridine, should be mentioned.

Among para-phenylenediamines, the following should be mentioned more especially:
para-phenylenediamine,
para-tolylenediamine,
2,6-dimethyl-para-phenylenediamine,
2,6-dimethyl-3-methoxy-para-phenylenediamine,
N-($\beta$-methoxyethyl)-para-phenylenediamine,
4-{N-[$\beta$-($\beta$-hydroxyethoxy)ethyl]amino}aniline,
4-[N,N-bis($\beta$-hydroxyethyl)amino]aniline,
4-[N-ethyl-N-(carbamylmethyl)amino]aniline,
as well as their salts.

Among para-aminophenols, the following should be mentioned more especially:
para-aminophenol,
2-methyl-4-aminophenol,
2-chloro-4-aminophenol,
2,6-dimethyl-4-aminophenol,
2,3-dimethyl-4-aminophenol,
2,5-dimethyl-4-aminophenol,
2-hydroxymethyl-4-aminophenol,
2-($\beta$-hydroxyethyl)-4-aminophenol,
as well as their salts.

Among ortho-phenylenediamines and orthoaminophenols which can be substituted on the ring or on the amine groups, 1-amino-2-hydroxybenzene, 6-methyl-1-hydroxy-2-aminobenzene and 4-methyl-1-amino-2-hydroxybenzene should be mentioned in particular.

Another subject of the invention consists of the dyeing compositions containing couplers in combination with the compounds (I).

Among the couplers, phenols, meta-diphenols, meta-aminophenols, meta-phenylenediamines, meta-acylaminophenols, meta-ureidophenols, meta-carbalkoxyaminophenols, $\alpha$-naphthol and couplers possessing an active methylene group such as $\beta$-keto compounds and pyrazolones may be mentioned in particular.

Among phenols, 2-isopropyl-5-methylphenol may be mentioned.

Among meta-diphenols, the following may be mentioned:
resorcinol,
2-methylresorcinol,
5-methylresorcinol,
2,4-dihydroxyphenoxyethanol,
resorcinol monomethyl ether,
2,4-dihydroxyanisole.

Among meta-aminophenols, the following may be mentioned:
meta-aminophenol,
2-methyl-5-aminophenol,
2-methyl-5-[N-($\beta$-hydroxyethyl)amino]phenol,
2-methyl-5-[N-($\beta$-mesylaminoethyl)amino]phenol,
2,6-dimethyl-3-aminophenol,
6-hydroxybenzomorpholine,
and their salts.

Among meta-phenylenediamines, the following may be mentioned:
meta-phenylenediamine,
2,4-diaminophenoxyethanol,
2,4-dimethoxy-1,3-diaminobenzene,
1,3,5-trimethoxy-2,4-diaminobenzene,
2,4-diaminoanisole,
6-aminobenzomorpholine,
{2-[N-($\beta$-hydroxyethyl)amino]-4-aminophenoxy}ethanol,
{4-[N-($\beta$-hydroxyethyl)amino]-2-aminophenoxy}ethanol,
2-amino-4-[N-($\beta$-hydroxyethyl)amino]anisole,
4,5-bis($\beta$-hydroxyethoxy)-1,3-diaminobenzene,
1-($\beta$-hydroxyethoxy)-2,4-diaminobenzene,
and their salts.

Among other couplers which are usable in the dyeing compositions of the invention, the following should be mentioned more especially:
3,4-methylenedioxyphenol,
3,4-methylenedioxyaniline,
2-bromo-4,5-methylenedioxyphenol,
2-chloro-4,5-methylenedioxyphenol,
2-methoxy-4,5-methylenedioxyaniline.

The dyeing compositions according to the invention can contain, in combination with the compounds of formula (I), the oxidation dye precursors and couplers defined above.

The total weight of oxidation dye precursors and/or couplers used in the dyeing compositions according to the invention is preferably from 0.1 to 7% by weight of the total weight of the dyeing composition.

The dyeing compositions according to the invention can also contain direct dyes such as azo dyes and anthraquinone dyes and nitro derivatives of the benzene series, which enable the colorations provided by the oxidation dye precursors and/or the couplers to be altered in hue or enriched with glints.

The pH of the dyeing composition is generally between 8 and 11, and preferably between 9 and 11. This pH is adjusted to the desired value using an alkalinizing agent such as ammonia solution, alkali metal carbonates or alkanolamines such as mono-, di- or triethanolamine.

The dyeing compositions according to the invention contain, in their preferred embodiment, anionic, cationic, nonionic or amphoteric surfactants or mixtures thereof. These surfactants are present in the compositions according to the invention in proportions of between 0.5 and 40% by weight, and preferably between 2 and 30% by weight, relative to the total weight of the composition.

These compositions can also contain organic solvents to solubilize compounds which might not be sufficiently soluble in water. Among these agents, there may be mentioned, by way of example, $C_1$–$C_8$ alcohols such as ethanol, isopropanol, benzyl alcohol and phenylethyl alcohol; glycerol; and glycols or glycol ethers such as 2-butoxyethanol, ethylene glycol, propylene glycol and diethylene glycol monoethyl ether and monomethyl ether; as well as similar products and mixtures thereof. The solvents are preferably present in a proportion of between 1 and 40% by weight, and especially between 2 and 30% by weight, relative to the total weight of the composition.

The thickeners which may be added to the compositions according to the invention are selected, in particular, from the group composed of sodium alginate, gum arabic, cellulose derivatives such as methylcellulose, hydroxyethylcellulose, hydroxypropylcellulose, hydroxymethylcellulose and carboxymethylcellulose, acrylic acid polymers and xanthan gum. Inorganic thickeners such as bentonite may also be used. These thickeners are preferably present in proportions of between 0.1 and 5% by weight, and especially between 0.5 and 3% by weight, of the total weight of the composition.

The compositions can contain antioxidants selected, in particular, from sodium sulphite, thioglycolic acid, sodium bisulphite, ascorbic acid and hydroquinone. These antioxidants are present in the composition in proportions of between 0.05 and 1.5% by weight of the total weight of the composition.

Other adjuvants which are usable according to the invention are, for example, penetrating agents, sequestering agents, buffers and fragrances.

The dyeing compositions according to the invention may be presented in various forms, in particular in the form of liquids, creams and gels, and in any other form suitable for carrying out a dyeing of keratinous fibres, and in particular human hair. They may also be packaged in aerosol cans in the presence of a propellant.

The dyeing compositions according to the invention are used in a hair dyeing process employing development with an oxidizing agent.

According to this process, the dyeing composition described above is mixed at the time of use with an oxidizing solution, in an amount sufficient to oxidize the oxidation dye precursors, and the mixture obtained is then applied on the hair.

The oxidizing solution contains, in aqueous solution, oxidizing agents selected from the group composed of hydrogen peroxide, urea peroxide and persalts such as ammonium persulphate. A hydrogen peroxide solution containing 6% by weight (20 volumes) is preferably used.

According to the dyeing process generally used, the mixture obtained is applied on the hair, at room temperature or at a temperature not exceeding 40° C., and left in place for 10 to 40 minutes, and preferably for 15 to 30 minutes, after which the hair is rinsed, washed with shampoo, rinsed again and dried.

Another process for employing the oxidation dye precursor of formula (I) according to the invention consists in dyeing the hair following a multi-step process, according to which the oxidation dye precursor of formula (I), optionally in the presence of other precursors, is applied in a first step by means of a composition defined above, and the coupler or couplers is/are applied in a second step. The oxidizing agent is present in the composition applied in the second step or alternatively applied on the hair itself in a third step; each of the compositions applied in the first and second steps and, if appropriate, the oxidizing agent applied in a third step are left in contact with the hair for 10 to 40 minutes, and preferably for 15 to 30 minutes, after which the hair is rinsed, washed with shampoo, rinsed again and dried.

The invention is illustrated by the application examples below.

APPLICATION EXAMPLES

Example 1

The following dyeing mixture is prepared:

| | |
|---|---|
| 2-Amino-5-acetamidophenol | 0.5 g |
| Hydroxyethylcellulose sold by UNION CARBIDE under the name CELLOSIZE WP 03 | 2.0 g |
| Ammonium lauryl sulphate | 5.0 g |
| 2-Butoxyethanol | 15.0 g |
| Ethanol, 96° strength | 6.0 g |
| Ammonium thiolactate | 0.8 g |
| Ammonia solution, specific gravity 22° Bé | 10.0 g |
| Water qs | 100.0 g |
| pH 10.4 | |

At the time of use, 80 g of "20 volumes" hydrogen peroxide (6% by weight) are added. When applied for 15 minutes at 35° C. on hair which is naturally 90% white, the mixture imparts thereto, after shampooing and rinsing, a pinkish beige coloration.

Example 2

The following dyeing mixture is prepared:

| | |
|---|---|
| 2-Amino-5-(ethoxycarbonylamino)phenol | 0.55 g |
| Crosslinked polyacrylic acid, sold by GOODRICH CHEMICAL under the name CARBOPOL 934 | 3.0 g |
| Ethanol, 96° strength | 11.0 g |
| 2-Butoxyethanol | 5.0 g |
| Trimethylcetylammonium bromide | 2.0 g |
| Ethylenediaminetetraacetic acid, sold under the name TRILON B | 0.2 g |
| Ammonia solution, specific gravity 22° Be | 10.0 g |
| Sodium bisulphite solution, specific gravity 35° Bé | 1.0 g |
| Water qs | 100.0 g |
| pH 9.1 | |

At the time of use, 70 g of "20 volumes" hydrogen peroxide are added. When applied for 20 minutes at 35° C. on bleached hair, the mixture imparts thereto, after shampooing and rinsing, an ashen beige coloration.

Example 3

The following dyeing mixture is prepared:

| | |
|---|---|
| 2-Amino-5-(benzylcarbonylamino)phenol | 0.69 g |
| Crosslinked polyacrylic acid, sold by GOODRICH CHEMICAL under the name CARBOPOL 934 | 3.0 g |
| Ethanol, 96° strength | 11.0 g |
| 2-Butoxyethanol | 5.0 g |
| Trimethylcetylammonium bromide | 2.0 g |
| Ethylenediaminetetraacetic acid, sold under the name TRILON B | 0.2 g |
| Ammonia solution, specific gravity 22° Bé | 10.0 g |
| Sodium bisulphite solution, specific gravity 35° Bé | 1.0 g |
| Water qs | 100.0 g |
| pH 9.1 | |

At the time of use, 100 g of "20 volumes" hydrogen peroxide are added. When applied for 20 minutes at 35° C. on bleached hair, the mixture imparts thereto, after shampooing and rinsing, a grey-toned deep pink coloration.

Example 4

The following dyeing mixture is prepared:

| | |
|---|---|
| 2-Amino-5-acetamidophenol | 0.5 g |
| p-Phenylenediamine | 0.27 g |
| Polyglycerolated oleyl alcohol containing 2 moles of glycerol | 4.5 g |
| Polyglycerolated oleyl alcohol containing 4 moles of glycerol | 4.5 g |
| Oxyethylenated oleylamine containing 12 moles of ethylene oxide, sold by ARMOON HESS CHEMICAL Ltd under the name ETHOMEEN O 12 | 4.5 g |
| Coconut diethanolamide, sold by HENKEL under the name COMPERLAN KD | 9.0 g |
| Propylene glycol | 4.0 g |
| 2-Butoxyethanol | 8.0 g |
| Ethanol, 96° strength | 6.0 g |
| Diethylenetriaminepentaacetic acid pentasodium salt, sold by PROTEX under the name MASQUOL DTPA | 2.0 g |

| | |
|---|---|
| Hydroquinone | 0.15 g |
| Sodium bisulphite solution, specific gravity 35° Bé | 1.3 g |
| Ammonia solution, specific gravity 22° Bé | 10.0 g |
| Water qs | 100.0 g |
| pH 10 | |

At the time of use, 100 g of "20 volumes" hydrogen peroxide are added. When applied for 20 minutes at 35° C. on hair which is naturally 90% white, the mixture imparts thereto, after shampooing and rinsing, a deep grey-purple coloration.

Example 5

The following dyeing mixture is prepared:

| | |
|---|---|
| 2-Amino-5-acetamidophenol | 0.55 g |
| p-Phenylenediamine | 0.27 g |
| Hydroxyethylcellulose, sold by UNION CARBIDE under the name CELLOSIZE WP 03 | 2.0 g |
| Ammonium lauryl sulphate | 5.0 g |
| 2-Butoxyethanol | 15.0 g |
| Ethanol, 96° strength | 6.0 g |
| Ammonium thiolactate | 0.8 g |
| Ammonia solution, specific gravity 22° Bé | 10.0 g |
| Water qs | 100.0 g |
| pH 10.4 | |

At the time of use, 100 g of "20 volumes" hydrogen peroxide are added. When applied for 20 minutes at 35° C. on hair which is naturally 90% white, the mixture imparts thereto, after shampooing and rinsing, a dark purple coloration.

Example 6

The following dyeing mixture is prepared:

| | |
|---|---|
| 2-Amino-5-(benzylcarbonylamino)phenol | 0.69 g |
| 4-Amino-2-(hydroxymethyl)phenol | 0.35 g |
| Crosslinked polyacrylic acid, sold by GOODRICH CHEMICAL under the name CARBOPOL 934 | 3.0 g |
| Ethanol, 96° strength | 11.0 g |
| 2-Butoxyethanol | 5.0 g |
| Trimethylcetylammonium bromide | 2.0 g |
| Ethylenediaminetetraacetic acid, sold under the name TRILON B | 0.2 g |
| Ammonia solution, specific gravity 22° Bé | 10.0 g |
| Sodium bisulphite solution, specific gravity 35° Bé | 1.0 g |
| Water qs | 100.0 g |
| pH 9 | |

At the time of use, 90 g of "20 volumes" hydrogen peroxide are added. When applied for 15 minutes at 35° C. on bleached hair, the mixture imparts thereto, after shampooing and rinsing, an old rose coloration.

Example 7

The following dyeing mixture is prepared:

| | |
|---|---|
| 2-Amino-5-(ethoxycarbonylamino)phenol | 0.55 g |
| N,N-Bis-(β-hydroxyethyl)-4-aminoaniline dihydrochloride | 0.67 g |
| Oxyethylenated nonylphenol containing 4 moles of ethylene oxide, sold by RHONE POULENC under the name CEMULSOL NP 4 | 12.0 g |
| Oxyethylenated nonylphenol containing 9 moles of ethylene oxide, sold by RHONE POULENC under the name CEMULSOL NP 9 | 15.0 g |
| Polyglycerolated oleyl alcohol containing 2 moles of glycerol | 1.5 g |
| Polyglycerolated oleyl alcohol containing 4 moles of glycerol | 1.5 g |
| Propylene glycol | 6.0 g |
| Ethylenediaminetetraacetic acid, sold under the name TRILON B | 0.12 g |
| Ammonia solution, specific gravity 22° Bé | 11.0 g |
| Water qs | 100.0 g |
| pH 10.1 | |

At the time of use, 100 g of "20 volumes" hydrogen peroxide are added. When applied for 20 minutes at 35° C. on bleached hair, the mixture imparts thereto, after shampooing and rinsing, a periwinkle blue coloration.

Example 8

The following dyeing mixture is prepared:

| | |
|---|---|
| 2-Amino-5-(ethoxycarbonylamino)phenol | 0.55 g |
| 4-Amino-2-methylphenol | 0.31 g |
| Hydroxyethylcellulose, sold by UNION CARBIDE under the name CELLOSIZE WP 03 | 2.0 g |
| Ammonium lauryl sulphate | 5.0 g |
| 2-Butoxyethanol | 15.0 g |
| Ethanol, 96° strength | 6.0 g |
| Ammonia solution, specific gravity 22° Bé | 10.0 g |
| Sodium bisulphite solution, specific gravity 35° Bé | 1.5 g |
| Hydroquinone | 0.15 g |
| Water qs | 100.0 g |
| pH 10.1 | |

At the time of use, 100 g of "20 volumes" hydrogen peroxide are added. When applied for 20 minutes at 35° C. on hair which is naturally 90% white, the mixture imparts thereto, after shampooing and drying, a pinkish beige coloration.

Example 9

The following dyeing mixture is prepared:

| | |
|---|---|
| 2-Amino-5-(benzylcarbonylamino)phenol | 0.69 g |
| 4-Amino-1-[(β-methoxyethyl)amino]benzene dihydrochloride | 0.60 g |
| Cetyl/stearyl alcohol, sold by CONDEA under the name ALFOL C 16/18 | 19.0 g |
| 2-Octyldodecanol, sold by HENKEL under the name EUTANOL G | 4.5 g |
| Cetyl/stearyl alcohol containing 15 moles of ethylene oxide, sold by HENKEL under the name MERGITAL C.S. | 2.5 g |
| Ammonium lauryl sulphate | 10.0 g |
| Cationic polymer possessing the following repeated unit: | 4.0 g |

$$\left[ \begin{array}{c} CH_3 \\ | \\ N^{\oplus}-(CH_2)_3-N^{\oplus}-(CH_2)_6 \\ | \\ CH_3 \quad Cl^{\ominus} \quad CH_3 \quad Cl^{\ominus} \end{array} \right]$$

| | |
|---|---|
| Benzyl alcohol | 2.0 g |
| Ammonia solution, specific gravity 22° Bé | 11 ml |
| Ethylenediaminetetraacetic acid, sold | |

-continued

| | |
|---|---|
| under the name TRILON B | 1.0 g |
| Sodium bisulphite solution, specific gravity 35° Bé | 1.2 g |
| Water | qs 100.0 g |
| pH 10.2 | |

At the time of use, 100 g of "20 volumes" hydrogen peroxide are added. When applied for 20 minutes at 35° C. on hair which is naturally 90% white, the mixture imparts thereto, after shampooing and rinsing, a navy blue coloration.

Example 10

The following dyeing mixture is prepared:

| | |
|---|---|
| 2-Amino-5-acetamidophenol | 0.506 g |
| (2,4-Diaminophenoxy)ethanol dihydrochloride | 0.602 g |
| Cetyl/stearyl alcohol, sold by CONDEA under the name ALFOL C 16/18 | 8.0 g |
| Sodium cetyl/stearyl sulphate, sold by HENKEL under the name CIRE DE LANETTE E | 0.5 g |
| Ethoxylated castor oil, sold by RHONE POULENC under the name CEMULSOL B | 1.0 g |
| Oleic diethanolamide | 1.5 g |
| Diethylenetriaminepentaacetic acid pentasodium salt, sold by PROTEX under the name MASQUOL DTPA | 2.5 g |
| Ammonia solution, specific gravity 22° Bé | 11.0 g |
| Water qs | 100.0 g |
| pH 10.4 | |

At the time of use, 100 g of "20 volumes" hydrogen peroxide are added. When applied for 20 minutes at 35° C. on hair which is naturally 90% white, the mixture imparts thereto, after shampooing and rinsing, a golden sandy coloration.

Example 11

The following dyeing mixture is prepared:

| | |
|---|---|
| 2-Amino-5-acetamidophenol | 0.69 g |
| 5-Amino-2-methylphenol | 0.31 g |
| Polyglycerolated oleyl alcohol containing 2 moles of glycerol | 4.5 g |
| Polyglycerolated oleyl alcohol containing 4 moles of glycerol | 4.5 g |
| Oxyethylenated oleylamine containing 12 moles of ethylene oxide, sold by ARMOON HESS CHEMICAL Ltd under the name ETHOMEEN O 12 | 4.5 g |
| Coconut diethanolamide, sold by HENKEL under the name COMPERLAN KD | 9.0 g |
| Propylene glycol | 4.0 g |
| 2-Butoxyethanol | 8.0 g |
| Ethanol, 96° strength | 6.0 g |
| Diethylenetriaminepentaacetic acid pentasodium salt, sold by PROTEX under the name MASQUOL DTPA | 2.0 g |
| Hydroquinone | 0.15 g |
| Sodium bisulphite solution, specific gravity 35° Bé | 1.3 g |
| Ammonia solution, specific gravity 22° Bé | 10.0 g |
| Water qs | 100.0 g |
| pH 10 | |

At the time of use, 100 g of "20 volumes" hydrogen peroxide are added. When applied for 20 minutes at 35° C. on bleached hair, the mixture imparts thereto, after shampooing and rinsing, an orange-salmon pink coloration.

Example 12

The following dyeing mixture is prepared:

| | |
|---|---|
| 2-Amino-5-acetamidophenol | 0.40 g |
| p-Aminophenol | 0.70 g |
| 4-Amino-1-[(β-methoxyethyl)amino]benzene dihydrochloride | 1.21 g |
| (2,4-Diaminophenoxy)ethanol dihydrochloride | 0.1 g |
| 6-Hydroxybenzomorpholine | 0.205 g |
| Oxyethylenated nonylphenol containing 4 moles of ethylene oxide, sold by RHONE POULENC under the name CEMULSOL NP 4 | 12.0 g |
| Oxyethylenated nonylphenol containing 9 moles of ethylene oxide, sold by RHONE POULENC under the name CEMULSOL NP 9 | 15.0 g |
| Polyglycerolated oleyl alcohol containing 2 moles of glycerol | 1.5 g |
| Polyglycerolated oleyl alcohol containing 4 moles of glycerol | 1.5 g |
| Propylene glycol | 6.0 g |
| Ethylenediaminetetraacetic acid, sold under the name TRILON B | 0.12 g |
| Ammonia solution, specific gravity 22° Bé | 11.0 g |
| Water qs | 100.0 g |
| pH 10.1 | |

At the time of use, 90 g of "20 volumes" hydrogen peroxide are added. When applied for 25 minutes at 35° C. on hair which is naturally 90% white, the mixture imparts thereto, after shampooing and rinsing, a charcoal grey coloration.

Example 13

The following dyeing mixture is prepared:

| | |
|---|---|
| 2-Amino-5-(ethoxycarbonylamino)phenol | 0.55 g |
| 2-Bromo-4,5-methylenedioxyphenol | 0.54 g |
| Hydroxyethylcellulose, sold by UNION CARBIDE under the name CELLOSIZE WP 03 | 2.0 g |
| Ammonium lauryl sulphate | 5.0 g |
| 2-Butoxyethanol | 15.0 g |
| Ethanol, 96° strength | 5.0 g |
| Diethylenetriaminepentaacetic acid pentasodium salt, sold by PROTEX under the name MASQUOL DTPA | 2.0 g |
| Triethanolamine | 5.0 g |
| Water qs | 100.0 g |
| pH 9 | |

At the time of use, 100 g of "20 volumes" hydrogen peroxide are added. When applied for 15 minutes at 35° C. on bleached hair, the mixture imparts thereto, after shampooing and rinsing, a golden blonde coloration.

Example 14

The following dyeing mixture is prepared:

| | |
|---|---|
| 2-Amino-5-(benzylcarbonylamino)phenol | 0.69 g |
| 2,5-Diaminopyridine dihydrochloride | 0.69 g |
| Oxyethylenated nonylphenol containing 4 moles of ethylene oxide, sold by RHONE POULENC under the name CEMULSOL NP 4 | 12.0 g |
| Oxyethylenated nonylphenol containing 9 moles of ethylene oxide, sold by RHONE POULENC under the name CEMULSOL NP 9 | 15.0 g |
| 8888Polyglycerolated oleyl alcohol containing 2 moles of glycerol | 1.5 g |
| Polyglycerolated oleyl alcohol containing 4 moles of glycerol | 1.5 g |

-continued

| | |
|---|---|
| Propylene glycol | 6.0 g |
| Ethylenediaminetetraacetic acid, sold under the name TRILON B | 0.12 g |
| Ammonia solution, specific gravity 22° Bé | 11.0 g |
| Water qs | 100.0 g |
| pH 10.3 | |

At the time of use, 100 g of "20 volumes" hydrogen peroxide are added. When applied for 25 minutes at 35° C. on hair which is naturally 90% white, the mixture imparts thereto, after shampooing and rinsing, a coppery light chestnut brown coloration.

Example 15

The following dyeing mixture is prepared:

| | |
|---|---|
| 2-Amino-5-acetamidophenol | 0.50 g |
| o-Aminophenol | 0.27 g |
| Oxyethylenated nonylphenol containing 4 moles of ethylene oxide, sold by RHONE POULENC under the name CEMULSOL NP 4 | 12.0 g |
| Oxyethylenated nonylphenol containing 9 moles of ethylene oxide, sold by RHONE POULENC under the name CEMULSOL NP 9 | 15.0 g |
| Polyglycerolated oleyl alcohol containing 2 moles of glycerol | 1.5 g |
| Polyglycerolated oleyl alcohol containing 4 moles of glycerol | 1.5 g |
| Propylene glycol | 6.0 g |
| Ethylenediaminetetraacetic acid, sold under the name TRILON B | 0.12 g |
| Ammonia solution, specific gravity 22° Bé | 11.0 g |
| Thioglycolic acid | 0.6 g |
| Water qs | 100.0 g |
| pH 10.3 | |

At the time of use, 80 g of "20 volumes" hydrogen peroxide are added. When applied for 15 minutes at 35° C. on hair which is naturally 90% white, the mixture imparts thereto, after shampooing and rinsing, a golden light chestnut brown coloration.

Example 16

The following dyeing mixture is prepared:

| | |
|---|---|
| 5-Acetamido-2-[(β-hydroxyethyl)amino]-phenol hydrochloride | 0.4 g |
| p-Phenylenediamine | 0.216 g |
| Polyglycerolated oleyl alcohol containing 2 moles of glycerol | 4.5 g |
| Polyglycerolated oleyl alcohol containing 4 moles of glycerol | 4.5 g |
| Oxyethylenated oleylamine containing 12 moles of ethylene oxide, sold by ARMOON HESS CHEMICAL Ltd under the name ETHOMEEN O 12 | 4.5 g |
| Coconut diethanolamide, sold by HENKEL under the name COMPERLAN KD | 9.0 g |
| Propylene glycol | 4.0 g |
| 2-Butoxyethanol | 8.0 g |
| Ethanol, 96° strength | 6.0 g |
| Diethylenetriaminepentaacetic acid pentasodium salt, sold by PROTEX under the name MASQUOL DTPA | 2.0 g |
| Hydroquinone | 0.15 g |
| Sodium bisulphite solution, specific gravity 35° Bé | 1.3 g |
| Ammonia solution, specific gravity 22° Bé | 10.0 g |
| Water qs | 100.0 g |
| pH 10 | |

At the time of use, 100 g of "20 volumes" hydrogen peroxide are added. When applied for 20 minutes at 35° C. on hair which is naturally 90% white, the mixture imparts thereto, after shampooing and rinsing, a dark purple-grey coloration.

Example 17

The following dyeing mixture is prepared:

| | |
|---|---|
| 5-Acetamido-2-(methylamino)phenol hydrochloride | 0.599 g |
| p-Phenylenediamine | 0.27 g |
| Hydroxyethylcellulose, sold by UNION CARBIDE under the name CELLOSIZE WP 03 | 2.0 g |
| Ammonium lauryl sulphate | 5.0 g |
| 2-Butoxyethanol | 15.0 g |
| Ethanol, 96° | 6.0 g |
| Ammonium thiolactate | 0.8 g |
| Ammonia solution, specific gravity 22° Bé | 10.0 g |
| Water qs | 100.0 g |
| pH 10.4 | |

At the time of use, 100 g of "20 volumes" hydrogen peroxide are added. When applied for 20 minutes at 35° C. on hair which is naturally 90% white, the mixture imparts thereto, after shampooing and rinsing, a dark purple coloration.

We claim:

1. A composition for dyeing keratinous fibers, especially human hair, comprising an effective concentration of a 5-substituted ortho-aminophenol of formula (I):

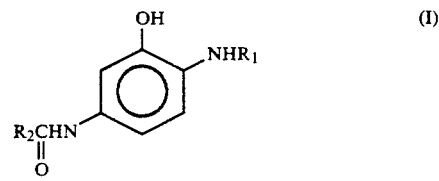

or an addition salt with an acid or a phenate of said 5-substituted ortho-aminophenols of formula (I), wherein:

$R_1$ is selected from the group consisting of a hydrogen atom, an alkyl radical having 1 to 4 carbon atoms and a hydroxyalkyl radical having 1 to 4 carbon atoms; and $R_2$, independently of $R_1$, is selected from the group consisting of an alkyl radical having 1 to 4 carbon atoms, an alkoxy radical having 1 to 4 carbon atoms and a benzyl radical;

said concentration is sufficient for dyeing said fibers; and further comprising an effective amount of at least one adjuvant selected from the group consisting of anionic, cationic, nonionic, and amphoteric surfactants, mixtures of anionic, cationic, nonionic, and amphoteric surfactants, organic solvents, thickeners, antioxidants, sequestering agents, buffers, and fragrances 2. The dyeing composition of claim 1, further comprising, in addition to said 5-substituted ortho-aminophenols, addition salts with acids or phenates thereof, an effective concentration of another oxidation dye precursor, which is not 5-substituted ortho-aminophenol of formula (I), wherein said effective concentration of said other precursor is sufficient, with said effective concentration of said 5-substituted ortho-aminophenols, addition salts with acids or phenates thereof, for dyeing said fibers.

3. The dyeing composition of claim 2, wherein said other oxidation dye precursors are selected from the group consisting of para-phenylenediamines, para-aminophenols, ortho-phenylenediamines, ortho-aminophenols and heterocyclic bases.

4. The dyeing composition of claim 1, further comprising an effective concentration of at least one coupler selected from the group consisting of couplers that, in the presence of an oxidizing agent, react with said 5-substituted ortho-aminophenol and any other oxidation dye precursors in said compositions to form dyes, wherein the concentration of said coupler is sufficient to dye said fibers a color that is different from the color which said fibers are dyed by said composition in the absence of said coupler, said any other oxidation dye precursors not being a 5-substituted ortho-aminophenol of formula (I).

5. The dyeing composition of claim 4, wherein the couplers are selected from the group consisting of phenols, meta-diphenols, meta-aminophenols, meta-phenylenediamines, meta-acylaminophenols, meta-ureido-phenols, meta-carbalkoxyaminophenols, α-naphthol and couplers possessing an active methylene group.

6. The composition of claim 5, wherein said couplers possessing an active methylene group are selected from the group consisting of β-keto compounds, pyrazolones, 3,4-methylenedioxyphenol, 3,4-methylenedioxyaniline, 2-bromo-4,5-methylenedioxyphenol1,2-chloro-4,5-methylenedioxyphenol and 2-methoxy-4,5-methylenedioxyaniline.

7. The dyeing composition of claim 1, wherein the concentration of said 5-substituted ortho-aminophenols of formula (I) is between 0.02 and 6% by weight relative to the total weight of the composition.

8. The dyeing composition of claim 4, wherein the total concentration of the oxidation dye precursors and the couplers is from 0.1 to 7% by weight relative to the total weight of the composition.

9. The dyeing composition of claim 1, wherein the pH of which is between 8 to 11.

10. The dyeing composition of claim 1, which is in the form of a liquid, cream or gel or packaged in an aerosol can in the presence of a propellant.

11. The dyeing composition of claim 3, wherein the oxidation dye precursor is 2,5-diaminopyridine.

12. A hair dyeing process, comprising mixing the composition of claim 1 with an oxidizing agent selected from the group consisting of hydrogen peroxide, urea peroxide and persalts, applying the resulting mixture on the hair for a time sufficient for said oxidizing agent to effect formation of a dye from said 5-substituted ortho-aminophenols, at a temperature not exceeding 40° C.

13. The method of claim 12, wherein said sufficient time is from 10 to 40 minutes.

14. The method of claim 12, further comprising rinsing the hair after the dyeing composition is applied and washing it with a shampoo.

15. A process for dyeing hair, comprising:
applying the dyeing composition of claim 1 on the hair;
and then, after 10 to 40 minutes, in a second step applying, for 10 to 40 minutes, a second composition that contains at least one coupler and an oxidizing agent at a concentration sufficient to effect dye formation, wherein:
said coupler is selected from the group consisting of couplers that, in the presence of the oxidizing agent, react with said 5-substituted ortho-aminophenols, addition salts with acids or phenates thereof, and any other oxidation dye precursors in said compositions to form dyes;
the concentration of said couplers is sufficient to dye said hair a color that is different from the color which said hair is dyed by said composition in the absence of said coupler; and
the temperature during said dyeing process does not exceed 40° C.

16. The process of claim 15, wherein said dye composition of claim 1 includes at least one oxidation dye precursor, which is not a 5-substituted ortho-aminophenol of formula (I), in addition to said 5-substituted ortho-aminophenol of formula (I).

17. The process of claim 15, further comprising rinsing and then shampooing the hair after said second step.

18. A process for dyeing hair, comprising:
(a) applying the dyeing composition of claim 1 on the hair for 10 to 40 minutes;
(b) applying, for 10 to 40 minutes, a second composition that contains at least one coupler; and
(c) applying a composition that contains an oxidizing agent at a concentration sufficient to effect dye formation, wherein:
said coupler is selected from the group consisting of couplers that, in the presence of the oxidizing agent, react with said 5-substituted ortho-aminophenols, addition salts with acids or phenates thereof, and any other oxidation dye precursors in said compositions to form dyes;
the concentration of said couplers is sufficient to dye said hair a color that is different from the color which said hair is dyed by said composition in the absence of said coupler; and
the temperature during said dyeing process does not exceed 40° C.

19. The process of claim 18, wherein said dye composition of claim 1 includes at least one oxidation dye precursor, which is not a 5-substituted ortho-aminophenol of formula (I), in addition to said 5-substituted ortho-aminophenol of formula (I).

20. The process of claim 18, further comprising rinsing and then shampooing the hair after said third step.

* * * * *